United States Patent [19]
Judson

[11] 3,964,487
[45] June 22, 1976

[54] UNCOMPLICATED LOAD-ADAPTING ELECTROSURGICAL CUTTING GENERATOR

[75] Inventor: Donald W. Judson, Simi Valley, Calif.

[73] Assignee: The Birtcher Corporation, Los Angeles, Calif.

[22] Filed: Dec. 9, 1974

[21] Appl. No.: 530,701

[52] U.S. Cl............................ 128/303.14; 128/422; 331/112
[51] Int. Cl.².............................................. A61N 3/00
[58] Field of Search.................. 128/303.14, 303.13, 128/303.17, 303.18, 422; 331/112

[56] References Cited
UNITED STATES PATENTS

| | | | |
|---|---|---|---|
| 2,816,230 | 12/1957 | Lindsay | 331/112 |
| 2,993,178 | 7/1961 | Burger | 128/303.14 |
| 3,057,356 | 10/1962 | Greatbatch | 128/422 |
| 3,530,338 | 9/1970 | Knabe | 331/112 |
| 3,601,126 | 8/1971 | Estes | 128/303.14 |
| 3,675,655 | 7/1972 | Sittner | 128/303.14 |
| 3,804,096 | 4/1974 | Gonser | 128/303.14 |
| 3,875,945 | 4/1975 | Friedman | 128/303.14 |
| 3,913,583 | 10/1975 | Bross | 128/303.14 |

Primary Examiner—Robert W. Michell
Assistant Examiner—Lee S. Cohen
Attorney, Agent, or Firm—Jackson & Jones

[57] ABSTRACT

A high frequency signal for cutting human tissue is generated by common-emitter configured oscillator circuit that is adapted to maintain the cutting signal relatively constant in spite of impedance variations in the load caused by variations in the conduction of the tissue being cut.

13 Claims, 2 Drawing Figures

3,964,487

UNCOMPLICATED LOAD-ADAPTING ELECTROSURGICAL CUTTING GENERATOR

BACKGROUND OF THE INVENTION

The present invention relates generally to improvements in cutting signal generators in electrosurgical devices, and more particularly pertains to new and improved oscillator circuitry utilized for generating high frequency cutting signals.

In the field of electrosurgical devices, it has been the practice to employ various types of electrosurgical generators suitable for generating cutting and coagulation currents. In some cases, the currents are provided by separate generators, one generator providing a cutting current and the other generator providing a coagulation current. In other cases, a single generator is utilized to provide both a cutting and coagulating current, or a combination of such currents. These prior art electrosurgical instruments, whether they used separate signal generators or one signal generator for producing the various types of signals required, either ignore the problem of the patient acting as a varying impedance load, or compensate for it by expensive and complicated means.

SUMMARY OF THE INVENTION

An object of this invention is to provide an electrosurgical device that provides a relatively constant tissue cutting signal, in spite of impedance changes in the load.

This object and the general purpose of this invention are accomplished by providing a transistor regenerative feedback oscillator-amplifier that has a load-coupling transformer in the collector circuit along with a feedback coupling winding to provide regenerative feedback to the base circuit which contains the frequency determining elements. The output signal from this oscillator-amplifier is applied to human tissue for cutting purposes.

BRIEF DESCRIPTION OF THE DRAWINGS

Other objects and many of the attendant advantages of this invention will be readily appreciated as it becomes better understood by reference to the following detailed description when considered in conjunction with the accompanying drawings, in which, like reference numerals designate like parts throughout the figures thereof and wherein.

DESCRIPTION OF THE PREFERRED EMBODIMENT

Figure 1:
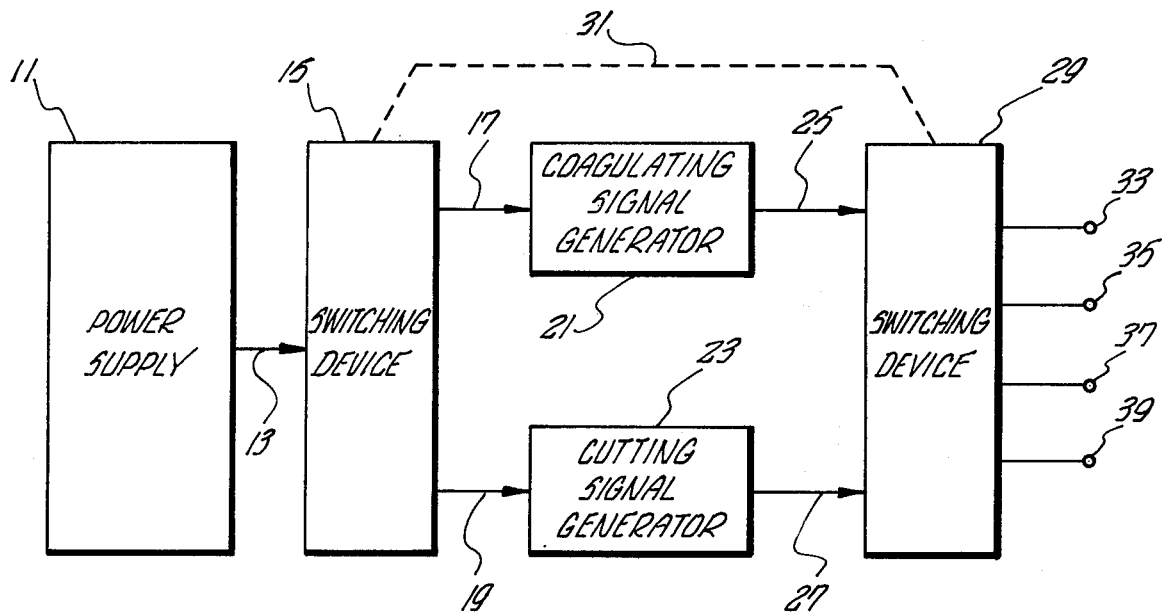
FIG. 1 is a block diagram illustration of a typical electrosurgical device.

Referring first to FIG. 1, the organization of an electrosurgical device that could utilize the cutting signal generator of the present invention is illustrated. A power supply 11 supplies DC power to a switching device 15 by way of cable 13. The switching device 15 may be mechanically or electromechanically actuated and is intercoupled electromechanically 31 with a switching device 29 at the output of a coagulating signal generator 21 and a cutting signal generator 23. Switching device 15 selectively supplies energy from the power supply to the coagulating signal generator 21 over cable 17.

The coagulating signal generator 21 may be a spark-gap oscillator that supplies high current, high frequency, damped oscillations over cable 25 to switching device 29. Switching device 29 may contain manually adjustable signal controls and path selection devices to, for example, switch the coagulating signal to line 33. Line 33 is then connected to a surgical instrument. Line 39 may be connected to the grounding or "indifferent" plate, contacting the patient and acts as a return path for the electrosurgical signal.

If a cutting signal is desired, switching device 15 supplies DC energy from the power supply 11 to the cutting signal generator 23 by way of cable 19. The cutting signal generator 23, as will be more fully explained hereinafter, is a medium frequency, high power oscillator-amplifier that generates a continuous signal. This signal is supplied to switching device 29 over cable 29. Switching device 29 connects this signal to a cutting terminal 35 which is connected to a surgical instrument (not shown). Electrosurgical devices such as, illustrated by FIG. 1, are well known in the prior art.

Figure 2:
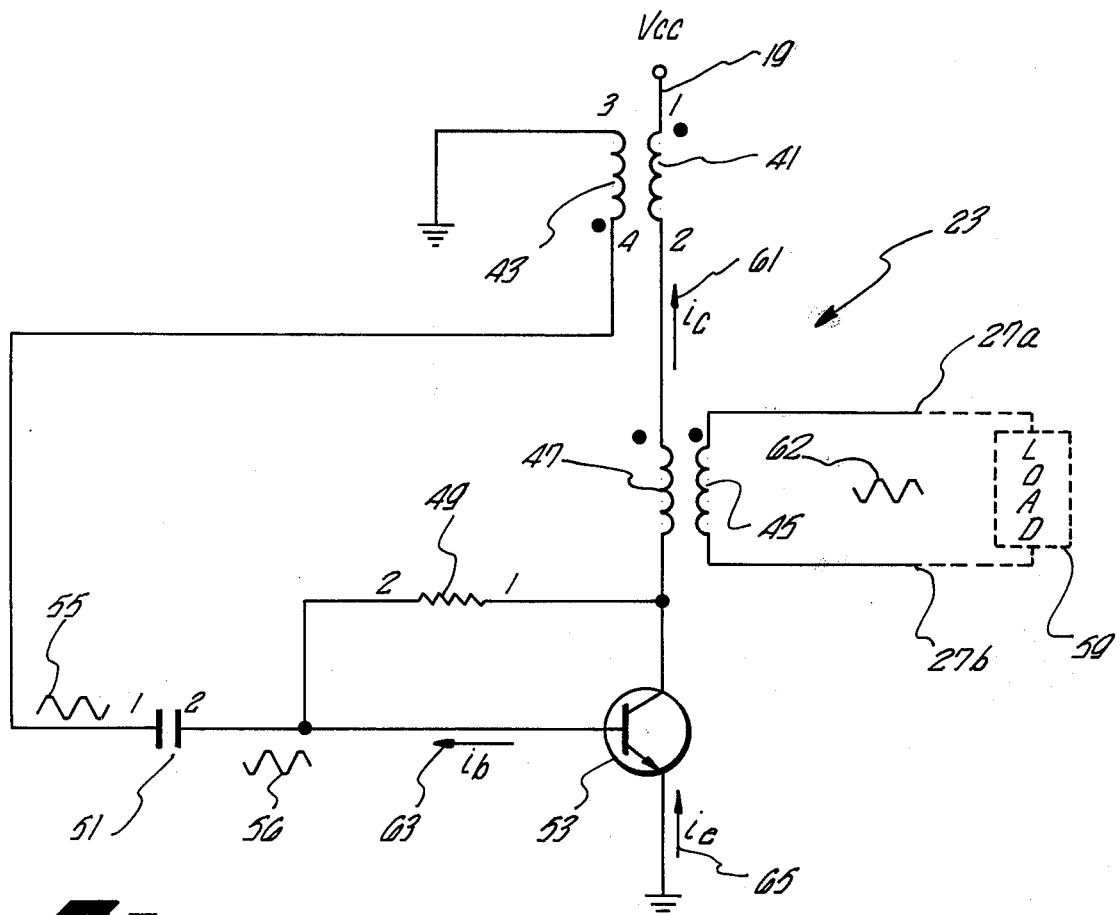
FIG. 2 is a circuit diagram of the preferred embodiment of the cutting signal generator of this invention.

The cutting signal generator 23, illustrated in FIG. 2, is uniquely designed to accommodate itself to the varying load conditions presented by the human body. The load 59 connected across the cutting signal generator output lines 27a, 27b may go from infinite impedance to zero impedance. However, practically speaking, when operating in the human body, the load can vary from several thousand ohms down to around 30 ohms.

The cutting signal generator 23 comprises an NPN transistor amplifier 53 shown to be configured in a commonemitter arrangement. The transistor amplifier is illustrated as being made up of one transistor. However, it should be understood that as many transistors as is necessary, connected in parallel, may be utilized to achieve the desired power output. The transistor amplifier 53 is connected as a regenerative feedback oscillator by way of a feedback transformer having a primary winding 41 and a secondary winding 43. Primary winding 47 of the load transformer is connected in series with the primary winding 41 of the feedback transformer. The secondary winding 45 of the load transformer is connected to the load 59 over output lines 27a, 27b.

The transistor amplifier 53 is biased by a resistor 49, which keeps the collector terminal at side 1 of resistor 49 positive with respect to the base at side 2 of the resistor 49. It should be understood that this NPN arrangement is only exemplary and that PNP transistors may be used as well, the biasing being rearranged appropriately.

A DC voltage from the power supply 11 is supplied to side 1 of the primary winding 41 over line 19. The secondary winding 43 of the transformer inversely couples the signal in the primary winding 41 to the base of transistor 53 by way of capacitor 51. One side of the secondary winding 43 is grounded, while the other side is connected to one side of capacitor 51.

The emitter of the transistor 53 is also grounded. The primary winding 47 and secondary winding 45 couple the signal in the collector circuit of transistor 53, without inversion, to the load.

The effective inductance of the winding 43 in the feedback loop and the capacitance of capacitor 51 in the feedback loop determine the time constant of the regenerative feedback oscillator circuit illustrated. In other words, the frequency of the output signal is determined by the value of inductor 43 and the value of capacitor 51.

When a DC power source is supplied to terminal 1 of primary coil 41, by way of line 19, the polarity of the primary winding will be plus at terminal 1 and minus at terminal 2. The polarity of primary winding 47 will be plus on top and minus on the bottom. The polarity of resistor 49 will be plus at terminal 1 and minus at terminal 2. This will bias the transistor 53 in a forward direction causing base current 63 to start flowing. When such base current starts flowing, collector current 61 and emitter current 65 will also start flowing in the direction shown by the arrows. The base current illustrated is actually electron flow. It should be understood that conventional current flows in a direction opposite to electron flow. This electron flow causes an expanding electromagnetic field in primary windings 47 and 41.

The electromagnetic field caused by primary winding 41 is coupled to secondary winding 43 which is wound to cause polarity inversion. Thereby, terminal 4 of winding 43 will be positive and terminal 3 will be negative when terminal 1 of primary winding 41 is positive and terminal 2 is negative. As electron flow increases in the collector circuit of transistor 53, the current induced in secondary winding 43, as a result of the expanding electromagnetic field in winding 41, will cause a positive charge build-up on plate 1 of capacitor 51. The other side or plate 2 of capacitor 51 will, therefore, have an increasing negative charge. This increasing negative charge at plate 2 acts to further bias the transistor 53 in the forward direction, causing an increase in base current 63, which in turn causes an increase in collector current 61 and emitter current 65.

This action will continue until the collector current 61 reaches a maximum as determined by the elements 41, 47 in the collector circuit and the transistor 53. At such time, since the current is no longer increasing, lack of an electromagnetic flux change in the primary winding 41 causes a lack of feedback current, by way of inductor 43 and capacitor 51. At such time, plate 1 of capacitor 51 has reached its maximum positive charge, as shown by the first half cycle of wave 55. The opposite plate 2 of capacitor 51, at this time has reached its maximum negative charge as shown by the first half cycle of wave 56.

The capacitor 51 will start discharging through inductor 43 to ground, according to the particular time constant dictated by the values of capacitor 51 and inductor 43. This discharge action causes the base current 63 to decrease, thereby decreasing the collector current 61 and the emitter current 65 of transistor 53. Since the collector current is now collapsing, the feedback coupling between primary winding 41 and the secondary winding 43, will aid this process, causing the capacitor to discharge until the transistor 53 is driven to cut-off as exhibited by practically zero emitter current and collector current.

At this time, plate 1 of capacitor 51 has reached its maximum negative charge, as shown by the second half cycle of wave 53. The other plate 2 of capacitor 51 has, in turn reached its maximum positive charge, as shown by the second half cycle of wave 56.

The biasing resistor 49 maintains the transistor in a forward bias condition, thereby causing base current 63 to again increase, in turn increasing emitter current 65 and collector current 61. This action causes a repeat of the first half cycle, as shown by waves 55 and 56.

Oscillation will continue in this manner until removal of the DC supply from side 1 of the primary winding 41 of the feedback transformer.

The primary winding 47 and the secondary winding 45 couple the load 59 into the collector circuit of the transistor 53. What in effect occurs by this arrangement, is the load impedance of the load 59 is reflected back into the primary 47 of the transformer so that, effectively, primary winding 47 may be replaced by the reflected impedance value of the load. Therefore, primary winding 47, secondary winding 45 and the load 59 can be thought of as a variable impedance in the collector circuit.

Bearing this in mind, it can be seen that as the value of the load impedance in the collector circuit of transistor 53 decreases, the collector current will increase. Assuming that the collector current 61 is in the increasing part of its cycle, a decreasing load impedance will tend to increase the collector current causing the voltage drop across the primary winding 41 to become larger. This increasing voltage drop is coupled from the primary winding 41 to the secondary winding 43, which in turn increases the feedback signal to the capacitor 51 thereby further forwarding biasing the transistor 53. This increased forward biasing increases the base current 63, the collector current 61 and the emitter current 65. The increasing collector current will compensate commensurately for the decreasing reflected impedance of the load to keep the voltage across the load from swinging sharply to a value below the desired minimum.

Assume now that the load impedance is increasing and the collector current is in an increasing cycle. The increasing impedance will cause the collector current to decrease. This causes the voltage drop across the primary winding 41 to decrease correspondingly, thereby decreasing the feedback signal and causing the charge on capacitor 51 to decrease. This decreases the forward bias of the transistor 53 which causes a decrease in the base current 63 and a commensurate decrease in the collector current 61. Here, the combination of a decreasing collector current with an increasing reflected load impedance keeps the voltage across the load from swinging sharply to a value above the desired maximum.

Besides stabilizing the voltage swings across the load, the oscillator of FIG. 2 controls the change in current through the load, thereby also preventing erratic swings in load current.

In summary, what has been disclosed is an electrosurgical device that utilizes an uncomplicated and inexpensive oscillator-amplifier circuit for generating tissue cutting signals. The oscillator-amplifier is designed to inexpensively adapt itself to impedance changes of the load. Obviously, many modifications and variations of the foregoing disclosure, as illustrated by the preferred embodiment, are possible in light of the above teachings. It is, therefore, to be understood that within the scope of the appended claims the invention may be practiced otherwise than as specifically described.

What is claimed is:

1. In an electrosurgical device having a power supply, a cutting signal generator driven by said power supply, and switching means for selecting the output signal of said generator for supply to a varying impedance cutting electrode load, the improvement therein being a cutting signal generator comprising:

amplifier means having an input and output circuit for supplying an output current in its output circuit which varies inversely with the impedance variation of said load; and means coupling the output current variation of said amplifier means to the input circuit of said amplifier means for causing said amplifier means to controllably reinforce the current variation in its output circuit.

2. The cutting signal generator of claim 1 wherein said coupling means include means for providing positive feedback to the input circuit of said amplifier means.

3. The cutting signal generator of claim 1 wherein said amplifier means comprises a transistor amplifier.

4. The cutting signal generator of claim 3 wherein said transistor amplifier comprises an NPN configured amplifier circuit.

5. The cutting signal generator of claim 4 further comprising a biasing resistor connected between the output and input circuit of said NPN transistor.

6. The cutting signal generator of claim 1 further comprising transformer means for coupling said output circuit to the load and transferring the voltage generated in the output circuit to the load.

7. The cutting signal generator of claim 1 wherein said coupling means comprises a transformer inversely coupling said output circuit to said input circuit.

8. The cutting signal generator of claim 7 further comprising a capacitor connecting said output-input coupling transformer to said input circuit, providing a desired time-constant for the cutting signal.

9. In an electrosurgical device having a power supply, a cutting signal generator driven by said power supply, and switching means for selecting the output signal of said generator for supply to a varying impedance cutting electrode load, the improvement therein being a cutting signal generator that maintains a relatively constant voltage across said varying impedance cutting electrode load, said cutting signal generator comprising:

amplifier means having an input circuit and an output circuit for amplifying the signal supplied to its input circuit;

a first coupling transformer having a primary and a secondary winding, said secondary winding being directly connected to said load and said primary winding being connected in the output circuit of said amplifier means; and a second transformer having a primary and secondary winding, said primary winding of said second transformer being connected to the primary winding of said first transformer and said secondary winding of said second transformer being connected in the input circuit of said amplifier means in a manner to inversely couple a signal generated in the primary winding of said second transformer to the input circuit of said amplifier means.

10. The electrosurgical device of claim 9, further comprising a capacitor connected between the secondary winding of said second transformer and the input circuit of said amplifier means.

11. The electrosurgical device of claim 10 wherein the primary and secondary winding of said second transformer provide voltage inversion between the two windings.

12. The electrosurgical device of claim 10 wherein said amplifier means comprises a transistor amplifier.

13. The electrosurgical device of claim 12 wherein said transistor amplifier comprises an NPN configured amplifier circuit.

* * * * *